United States Patent [19]

Daher

[11] Patent Number: 4,657,550
[45] Date of Patent: Apr. 14, 1987

[54] BUTTRESSING DEVICE USABLE IN A VERTEBRAL PROSTHESIS

[76] Inventor: Youssef H. Daher, 9 Ter Avenue de la Gaillarde, 34000 Montpellier, France

[21] Appl. No.: 819,353

[22] Filed: Jan. 16, 1986

[51] Int. Cl.[4] ............................ A61F 2/44; A61F 5/04
[52] U.S. Cl. .......................................... 623/17; 128/69; 128/92 YM
[58] Field of Search .............. 623/17, 18; 128/92 YM, 128/69, 84 R

[56] References Cited

U.S. PATENT DOCUMENTS

| | | | |
|---|---|---|---|
| 4,289,123 | 9/1981 | Dunn | 128/84 R |
| 4,401,112 | 8/1983 | Rezaian | 623/17 X |
| 4,553,273 | 11/1985 | Wu | 623/18 |

Primary Examiner—Ronald L. Frinks
Attorney, Agent, or Firm—Marshall, O'Toole, Gerstein, Murray & Bicknell

[57] ABSTRACT

A device for maintaining the normal spacing between two vertebrae defining, in the vertebral column, the ends of a cavity resulting from the removal of at least a part of a vertebra comprises two bases each having means for anchorage in one of said end vertebrae; and adjustable buttressing means connecting said bases together.

8 Claims, 2 Drawing Figures

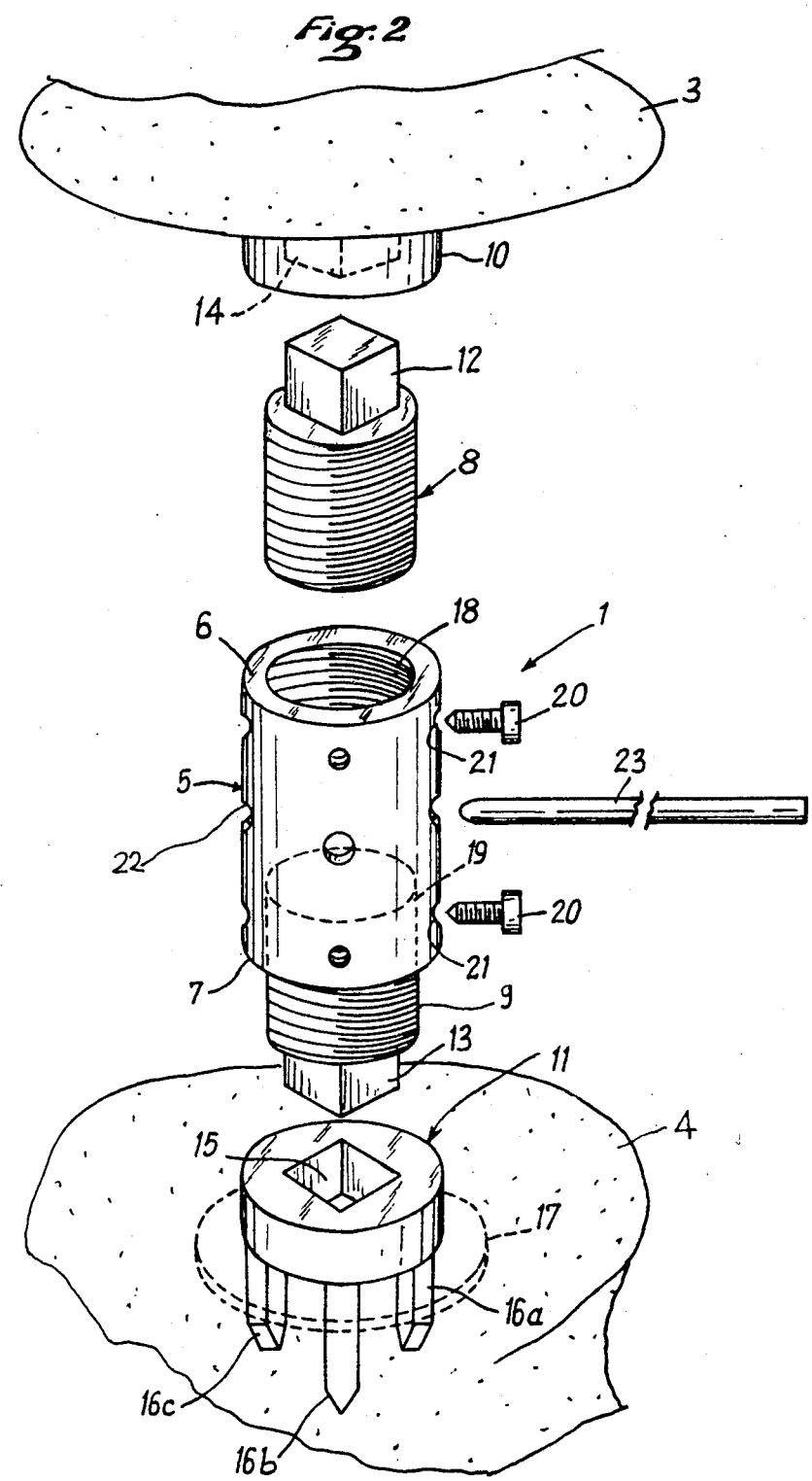

BUTTRESSING DEVICE USABLE IN A VERTEBRAL PROSTHESIS

BACKGROUND OF THE INVENTION

1. Field of the Invention

The present invention relates to a device for maintaining the normal spacing between two vertebrae defining, in the vertebral column, the ends of a cavity resulting from the elimination of at least a part of a vertebra.

In a certain number of cases it proves necessary to ablate a vertebra, at least partially, in a patient. In fact, the fracture of a vertebra by shattering, particularly in the dorso-lumbar region, may cause compression of the spinal cord resulting in serious neurological troubles which may cause paraplegia. Similarly, a vertebral tumour whatever its level, may cause similar neurological problems. In both cases, recourse is had to removing the damaged vertebra, which must of course be replaced by a prosthesis. In the first case, a bone graft (internal prosthesis) is used which will be revascularized in a period of time between 6 and 9 months; in the second case, it is preferred to use a prosthesis made from a synthetic material, such for example as a resin.

2. Description of the Prior Art

It is known to use, as vertebral prosthesis frame, a buttress formed of a threaded rod both ends of which are housed in holes drilled in the vertebrae defining, in the spinal column, the ends of the cavity resulting from the removal, at least partial, of the vertebra. The threaded rod is held in these holes by nuts bearing on the end of vertebrae. The bone or synthetic prosthesis is then placed about this support.

A device of this type has however a certain number of disadvantages. On the one hand, such a buttress is relatively fragile considering the very high stresses to which it may be subjected. Furthermore, it is necessary to use a rod whose length is greater than the spacing between the end vertebrae, which causes difficulties in positioning.

The purpose of the present invention is therefore to overcome these drawbacks by proposing a vertebral prosthesis buttressing device whose height is adjustable, which facilitates positioning thereof, and which is designed so that it may withstand all the mechanical stresses to which it is likely to be subjected.

SUMMARY OF THE INVENTION

To this end, in accordance with the present invention, the device for maintaining normal spacing between two vertebrae defining, in the vertebral column, the ends of a cavity resulting from the removal of at least a part of a vertebra, is characterized in that it comprises two bases each having means for anchoring in one of said end vertebrae, and adjustable buttressing means connecting said bases together.

The device of the invention thus allows the whole height of the removed vertebral body to be made up without requiring a complementary surgical operation. Furthermore, since the device takes up no more than 30% of the circumference of the vertebra, bone grafts may be readily put in place for a natural consolidation.

According to another feature of the invention, the above mentioned buttressing means comprise at least two elements able to be moved, parallel to the general axis of the vertical column, with respect to each other; more particularly along the axis common to said elements.

In particular, the above mentioned buttressing means comprise two elements movable, parallel to the general axis of the vertebral column, with respect to each other by means of a connecting piece and more particularly in said connecting piece.

Said connecting piece may be substantially in the form of a nut, and the above mentioned buttressing elements substantially in the form of threaded rods.

Advantageously, the free end of at least one of said buttressing elements is able to be connected to the corresponding base by a mortice and tenon type fitting. In particular, said free end is in the form of a tenon which may be fitted in a mortice of corresponding section provided in said base. Said tenon may have a polygonal cross section, more particularly at least substantially square.

According to yet another characteristic of the invention, said anchorage means are formed by a certain number of anchorage points whose lower end has substantially a bevelled shape. Three anchorage points may be more especially divided disposed at about 120° with respect to each other; whereas a washer, fitted more particularly in said anchorage points, may be provided under said base.

According to yet another feature of the invention, the threads at both ends of said connecting piece are in opposite directions; and at the two ends of said connecting piece means are further provided for locking said buttressing elements in position.

Finally, in the central part of said connecting piece a certain number of orifices are provided for introducing means, such as a rod, for facilitating rotation of said piece.

BRIEF DESCRIPTION OF THE DRAWINGS

The invention will be better understood and other details, advantages and characteristics thereof will be clearer from the following explanatory description made with reference to the accompanying schematical drawings, given solely by way of example of one presently preferred embodiment of the invention, and in which:

FIG. 2 is an exploded perspective view of the device of the invention, one of the buttressing elements being shown inserted in the connecting piece and the other element outside said piece, solely for the purpose of illustration.

DESCRIPTION OF THE PREFERRED EMBODIMENT

Figure 1:
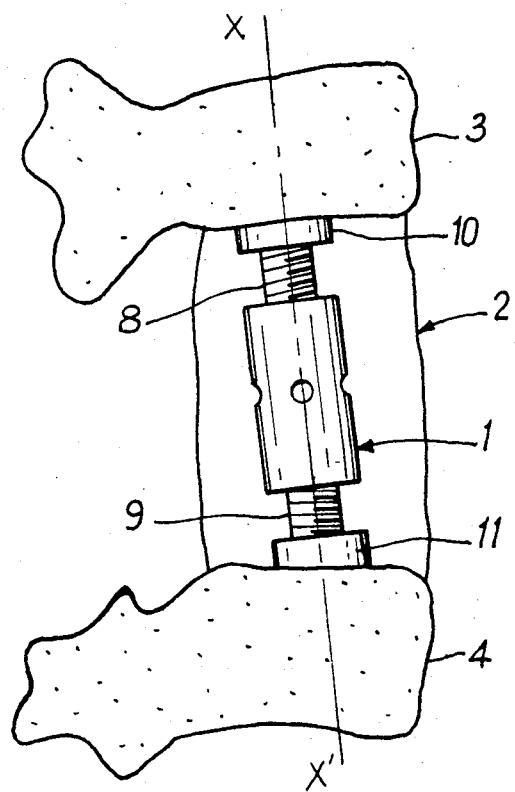
FIG. 1 is a schematical perspective view of the device of the invention disposed between two vertebrae.

Referring particularly to FIG. 2, the device of the invention for maintaining the normal spacing between two vertebrae 3, 4 defining, in the vertebral column, the ends of a cavity resulting from the removal of at least a part of a vertebra, comprises two bases 10, 11 each having a means for anchoring in one of the end vertebrae 3, 4; and adjustable buttressing means 1 connecting the bases 10, 11 together.

The buttressing means 1 comprise more particularly two elements 8, 9 able to be moved with respect to each other parallel to the axis of the vertebral column; they are more particularly movable along the axis X,X' common to said elements, in a connecting piece 5.

In the embodiment illustrated, the connecting piece 5 is substantially in the form of a nut and is tapped, at least in the vicinity of its two ends 6, 7, so as to receive said buttressing elements 8, 9 substantially in the form of threaded rods.

The free end of the buttressing elements 8, 9, i.e. the end opposite the corresponding base 10, 11, is able to be connected to said corresponding base by a mortice and tenon type fitting. In particular, it may be in the form of a tenon 12, 13 which may be fitted in a mortice 14, 15 of corresponding section provided in one of the bases 10, 11. For avoiding any risk of rotation of the buttressing means in the bases, the tenons 12, 13 have advantageously a polygonal, more particularly square, cross section.

Each base is formed from anchorage means comprising a certain number of anchorage points 16a, 16b, 16c whose lower end is substantially in the form of a bevel. As illustrated, three anchorage points may be provided for each base disposed at about 120° with respect to each other.

Furthermore, so as to distribute the loads supported by the bases, a washer 17, more particularly fitted in the above mentioned anchorage points, is provided under each base.

It will moreover be noted that the threads 18 19 provided at both ends of the connecting piece 5 are of opposite directions, whereas at both ends of the connecting piece 5 bores 21 are provided in which are housed screws 20 for locking the buttressing elements 8, 9 in position.

Finally, in the central part of the connecting piece 5 a certain number of orifices 22 are provided for introducing a rod 23 for facilitating rotation of said piece.

A description will now be given of how to position the buttressing device of the invention.

A cavity having been created in the vertebral column of a patient by removing at least a part of a vertebra following a fracture or a vertebral tumour, the bases 10, 11 with their washers are fixed in the two vertebrae defining said cavity; then, between these latter is placed the connecting piece 5 into which the buttressing elements 8, 9 are screwed. By rotating the connecting piece 5 (using more particularly a rod 23), and because the two threads 18 19 at the ends of the connecting piece are of opposite directions, the level of the part of the two buttressing elements projecting from the connecting piece may be set to the required height (corresponding to the effective height of the missing vertebra), while fitting the tenon of each buttressing element into the mortice of the corresponding base. Rotation of the connecting piece 5 is of course continued until the whole of the buttressing device is jammed into position. This assembly may possibly be consolidated by using the locking screws 20.

Once the buttressing device is in position, it may be embedded in a prosthesis 2, either a bone or synthetic prosthesis, in the usual way.

What is claimed is:

1. A device for maintaining the normal spacing between two vertebrae defining, in the vertebral column, the ends of a cavity resulting from the removal of at least a part of a vertebra, said device comprising:

buttressing means including a connecting piece in the form of an elongated nut and a pair of threaded rods engaging said nut, each rod having a free end extending from said nut, said rods being movable with respect to each other in the connecting piece in a direction parallel to the axis of the vertebral column, and anchorage means including a base provided with a plurality of anchorage points, said base being attached to each of said free ends for anchoring said device between said vertebrae, at least one of said bases being removably attached to its associated free end by connecting means including a tenon on one of said free end and said associated base and a mortice on the other of said free end and said base, said mortice and said tenon having corresponding cross-sections such that said tenon fits into said mortice.

2. The device of claim 1 wherein said free end is in the form of a tenon and said base is provided with a mortice of corresponding cross-section.

3. A device in accordance with claim 2, wherein said tenon has a polygonal cross-section.

4. A device in accordance with claim 3, wherein said tenon has a cross-section which is at least substantially square.

5. A device in accordance with claim 1 further including a washer adjacent each base and fitted in said anchorage points.

6. A device in accordance with claim 1, wherein said connecting piece is provided with internal threads of opposite directions.

7. A device in accordance with claim 1, wherein means are provided at both ends of said connecting piece for locking said buttressing elements in position.

8. A device in accordance with claim 1, wherein a plurality of orifices are provided in said connecting piece adapted to receive means for rotating said connecting piece.

* * * * *